United States Patent
Jaber et al.

(10) Patent No.: US 11,944,471 B2
(45) Date of Patent: Apr. 2, 2024

(54) OPTIMIZING THE POSITIONING OF A PATIENT ON A PATIENT COUCH FOR MEDICAL IMAGING

(71) Applicant: Siemens Healthcare GmbH, Erlangen (DE)

(72) Inventors: Jumana Jaber, Erlangen (DE); Carsten Thierfelder, Pinzberg (DE); Andreas Wimmer, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/350,049

(22) Filed: Jun. 17, 2021

(65) Prior Publication Data

US 2021/0393218 A1 Dec. 23, 2021

(30) Foreign Application Priority Data

Jun. 23, 2020 (DE) ...................... 10 2020 207 753.3

(51) Int. Cl.
*A61B 6/04* (2006.01)
*A61B 6/00* (2006.01)
(Continued)

(52) U.S. Cl.
CPC ............ *A61B 6/0407* (2013.01); *A61B 6/469* (2013.01); *A61B 6/503* (2013.01)

(58) Field of Classification Search
CPC .. A61B 6/469; A61B 6/08; A61B 6/54; A61B 6/465; A61B 6/545; A61B 6/544;
(Continued)

(56) References Cited

U.S. PATENT DOCUMENTS 7,869,562 B2 * 1/2011 Khamene ............... A61B 6/583
209/207
8,235,530 B2 * 8/2012 Maad ........................ G06T 7/74
600/595
(Continued)

FOREIGN PATENT DOCUMENTS

CN 104161533 A 11/2014
DE 102007017794 B3 12/2008
(Continued)

*Primary Examiner* — Dani Fox
*Assistant Examiner* — Soorena Kefayati
(74) *Attorney, Agent, or Firm* — Harness, Dickey & Pierce, P.L.C.

(57) ABSTRACT

A computer-implemented method is for operating a medical imaging system. The imaging system includes an imaging unit and a positioning apparatus for positioning an examination object. In an embodiment, the method includes ascertainment of object information relating to the examination object; determination of a region of interest for the examination object, the region of interest being defined as a region of the examination object to be examined by the imaging unit in the context of an examination to be performed; arrival at a determination concerning a positional state of the examination object relative to the positioning apparatus and, to be precise, based on the region of interest and the object information; and provision of user output for a user of the imaging system based on the determination.

18 Claims, 6 Drawing Sheets

(51) Int. Cl.
*A61B 6/46* (2024.01)
*A61B 6/50* (2024.01)

(58) Field of Classification Search
CPC ....... A61B 6/542; A61B 6/461; A61B 6/0492; A61B 6/0487; A61B 6/0407; A61B 6/488; A61B 6/035; A61B 6/04; A61B 6/032; A61B 6/503
See application file for complete search history.

(56) References Cited

U.S. PATENT DOCUMENTS

| | | | | |
|---|---|---|---|---|
| 9,642,584 | B2* | 5/2017 | Niebler | A61B 6/4441 |
| 2004/0081341 | A1* | 4/2004 | Cherek | A61B 6/08 |
| | | | | 382/128 |
| 2007/0053503 | A1* | 3/2007 | Zelnik | A61B 6/04 |
| | | | | 378/205 |
| 2011/0135190 | A1* | 6/2011 | Maad | A61B 6/0407 |
| | | | | 382/154 |
| 2013/0342851 | A1* | 12/2013 | Dresel | G01B 11/24 |
| | | | | 356/601 |
| 2015/0003674 | A1* | 1/2015 | Eun | A61B 6/08 |
| | | | | 382/103 |
| 2015/0104092 | A1* | 4/2015 | Flohr | A61B 6/08 |
| | | | | 382/131 |
| 2015/0208989 | A1* | 7/2015 | Rackow | A61B 6/488 |
| | | | | 378/206 |
| 2015/0272505 | A1* | 10/2015 | Schmidt | A61B 5/706 |
| | | | | 600/407 |
| 2015/0351709 | A1* | 12/2015 | Dirauf | A61B 6/0492 |
| | | | | 378/206 |
| 2016/0073979 | A1* | 3/2016 | Braun | A61B 6/0492 |
| | | | | 5/601 |
| 2016/0074004 | A1* | 3/2016 | Braun | G06F 3/017 |
| | | | | 378/205 |
| 2016/0092078 | A1* | 3/2016 | Braun | A61B 34/00 |
| | | | | 348/46 |
| 2016/0128666 | A1* | 5/2016 | Grasruck | A61B 6/467 |
| | | | | 378/19 |
| 2016/0174930 | A1* | 6/2016 | Braun | A61B 6/0407 |
| | | | | 378/205 |
| 2016/0220219 | A1* | 8/2016 | Lalena | A61B 6/4464 |
| 2016/0367169 | A1* | 12/2016 | Hardie | A61B 5/743 |
| 2016/0374639 | A1* | 12/2016 | Becker | A61B 6/08 |
| | | | | 378/95 |
| 2017/0000446 | A1* | 1/2017 | Brinker | A61B 6/544 |
| 2017/0071557 | A1 | 3/2017 | Groten et al. | |
| 2017/0112416 | A1* | 4/2017 | Hao | A61B 6/032 |
| 2017/0196525 | A1* | 7/2017 | Kim | A61B 90/39 |
| 2017/0200317 | A1* | 7/2017 | Hannemann | A61B 5/00 |
| 2017/0224298 | A1* | 8/2017 | Hannemann | A61B 6/469 |
| 2017/0347974 | A1* | 12/2017 | Izumo | G01N 23/046 |
| 2017/0354385 | A1* | 12/2017 | Lerch | A61B 6/4435 |
| 2018/0092541 | A1* | 4/2018 | Lerch | A61B 5/0062 |
| 2018/0296178 | A1* | 10/2018 | Chang | G06T 7/73 |
| 2019/0159740 | A1* | 5/2019 | Van Ammel | A61B 6/545 |
| 2019/0183439 | A1* | 6/2019 | Joerger | A61B 6/545 |
| 2019/0343479 | A1* | 11/2019 | Sato | A61B 6/06 |
| 2020/0237334 | A1* | 7/2020 | Koken | G06T 7/0014 |
| 2020/0268339 | A1* | 8/2020 | Hao | G06T 7/0014 |
| 2020/0390406 | A1* | 12/2020 | Xu | A61B 6/547 |
| 2021/0265057 | A1* | 8/2021 | Karanam | A61B 6/5294 |

FOREIGN PATENT DOCUMENTS

| | | |
|---|---|---|
| DE | 102014205702 A1 | 10/2015 |
| DE | 102014218558 A1 | 3/2016 |
| DE | 102014219674 B3 | 3/2016 |
| EP | 3838157 A1 | 6/2021 |
| WO | WO 2017109130 A1 | 6/2017 |

* cited by examiner

OPTIMIZING THE POSITIONING OF A PATIENT ON A PATIENT COUCH FOR MEDICAL IMAGING

PRIORITY STATEMENT

The present application hereby claims priority under 35 U.S.C. § 119 to German patent application number DE 102020207753.3 filed Jun. 23, 2020, the entire contents of which are hereby incorporated herein by reference.

FIELD

Example embodiments of the invention generally relate to a medical imaging system and a method for operating the same.

BACKGROUND

When a patient is examined by medical imaging systems, the patient is typically arranged on a patient couch that is moved relative to the actual imaging unit of the imaging system during the examination. If, for example, an examination is to be carried out using computed tomography (CT) or magnetic resonance (MR), the patient is moved via the patient couch along the system axis of the CT or MR device through an opening in what is called the gantry.

In practice, difficulties can arise due to the fact that the travel range of the patient couch is limited relative to the imaging unit. As a result, unfavorable positioning of the patient on the patient couch cannot be compensated at will. If, for example, a thorax/lung scan is to be carried out on the patient for which the patient is to be moved feet-first into the CT device, it is possible that the region of interest (thorax/lung) cannot be brought completely into the scanning range of the CT device if, for example, the patient has been placed too far toward the head end of the patient couch. This results in incorrect measurements the repetition of which is not only uneconomical, but above all it also increases the patient's individual radiation exposure.

The situation is further complicated by the fact that individual patients may have very different requirements regarding placement on the patient couch. For example, it may be the case that in principle very large patients have to be positioned in a different manner than patients of a normal size (for example "head first" instead of feet first). However, for other patients a head-first position may in turn be ruled out due to claustrophobic anxiety. The patient's body circumference may also require a specially adapted arrangement on the patient couch. Thus, depending on the body circumference, it may be necessary to lower or raise the patient couch in order to be able to align the patient with the system axis. Since the horizontal travel range of many patient couches depends on the selected height setting, this must also be taken into account when arranging the patient on the patient couch.

In summary, therefore, there is a wide variety of basic circumstances that have to be taken into account when placing a patient correctly on a patient couch, but which are often difficult for the user (for example: a technical assistant, a physician or a radiologist or the actual patient) to assess from a causal point of view. For some cases, assistance is provided by markings applied to the patient couch which may indicate a suitable position for some standard cases. Due to the variety of different examinations (with different regions of interest) and the aforementioned basic circumstances relating to an individual patient, in practice, if they are any help at all, such markings can only provide clues.

As a result, positioning of the patient on the patient couch is frequently based on "trial and error". The patient is experimentally positioned on the patient couch and then the examination position approached on a test basis. To keep the patient's exposure to radiation as low as possible, it is preferable for no measurement to be performed. Therefore, it requires a certain amount of experience to assess the positional state of the patient on this basis and, if necessary, organize a suitable repositioning. As a result, it is not possible to completely rule out unwanted incorrect measurements. In addition, such a procedure increases the occupancy times of the device and causes agitation in patients who may already be tense.

SUMMARY

At least one embodiment of the present invention provides a method and a corresponding apparatus to assist the finding of a suitable positional state of a patient on a patient positioning apparatus in the context of an imaging medical examination while reducing the patient's exposure to radiation and improving efficiency.

Embodiments of the invention are directed to a method, an imaging system or a computer program product. Advantageous developments are disclosed in the claims.

According to one embodiment of the invention, a computer-implemented method for operating a medical imaging system is provided. The imaging system includes an imaging unit and a positioning apparatus for positioning an examination object. The method includes a plurality of steps. One step is directed at the ascertainment of object information relating to the examination object. A further step is directed at the determination of a region of interest for the examination object, wherein the region of interest is defined as a region of the examination object to be examined by the imaging unit in the context of an examination to be performed. A further step is directed at arriving at a determination concerning a positional state of the examination object relative to the positioning apparatus based on the region of interest and the object information. A further step is directed at the provision of user output for a user of the imaging system based on the determination.

According to a further embodiment of the present invention, a medical imaging system is provided. The medical imaging system includes an imaging unit, a positioning apparatus for positioning an examination object, and a processing unit. Herein, the processing unit is embodied to determine object information on the examination object. The processing unit is further embodied to determine a region of interest, wherein the region of interest is defined as a region of the examination object to be examined by the imaging unit. The processing unit is further embodied, based on the object information and the region of interest, to arrive at a determination relating to a positional state of the examination object on the positioning apparatus. Furthermore, the processing unit is embodied to generate user output based on the determination.

In a further embodiment, the invention relates to a computer program product which comprises a program and can be loaded directly into a memory of a programmable computing unit and includes program segments, for example libraries and auxiliary functions, in order to execute a method to control an imaging system in particular according to the aforementioned embodiment when the computer program product is executed.

At least one embodiment is directed to a computer-implemented method for operating a medical imaging system, the imaging system including an imaging device and a positioning apparatus to position an examination object, the method comprising:

ascertaining object information relating to the examination object;

determining a region of interest for the examination object, the region of interest being a region of the examination object to be examined by the imaging device in context of an examination to be performed;

arriving at a determination concerning a positional state of the examination object, relative to the positioning apparatus, based on the region of interest determined and the object information ascertained; and providing user output, for a user of the imaging system, based on the determination.

At least one embodiment is directed to a medical imaging system, comprising:

an imaging device;

a positioning apparatus to position an examination object; and at least one processor configured to determine object information on the examination object, determine a region of interest, the region of interest being defined as a region of the examination object to be examined by the imaging device during an examination to be performed, arrive at a determination relating to a positional state of the examination object on the positioning apparatus based on the object information and the region of interest determined, and generate user output based on the determination.

At least one embodiment is directed to a non-transitory computer program product storing a program, directly loadable into a memory of a programmable computing device, including program segments for executing the method of an embodiment when the program is executed in the computing device.

BRIEF DESCRIPTION OF THE DRAWINGS

Further special features and advantages of the invention will become evident from the following explanations of example embodiments with reference to schematic drawings. Modifications named in this context can in each case be combined with one another in order to form new embodiments. In different figures, the same reference characters are used for the same features.

The figures show.

DETAILED DESCRIPTION OF THE EXAMPLE EMBODIMENTS

Figure 1:
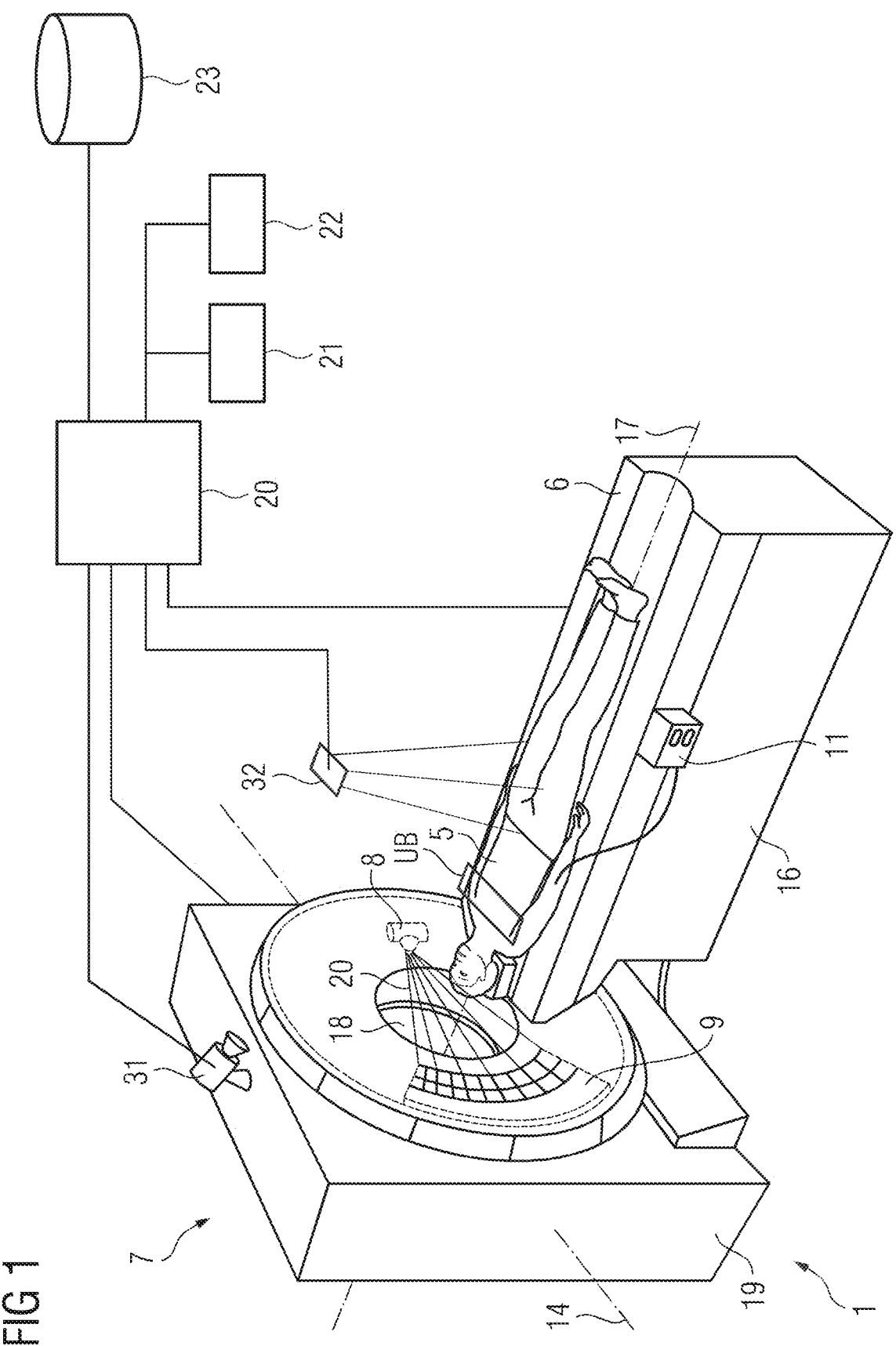
FIG. 1 a schematic depiction of an embodiment of the suggested imaging system, FIG. 2 a schematic depiction of an embodiment of a suggested method for controlling a medical imaging system, and FIGS. 3 to 10 schematic depictions of user outputs concerning a positional state of an examination object with respect to an examination to be performed on the examination object via the imaging system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to one embodiment of the invention, a computer-implemented method for operating a medical imaging system is provided. The imaging system includes an imaging unit and a positioning apparatus for positioning an examination object. The method includes a plurality of steps. One step is directed at the ascertainment of object information relating to the examination object. A further step is directed at the determination of a region of interest for the examination object, wherein the region of interest is defined as a region of the examination object to be examined by the imaging unit in the context of an examination to be performed. A further step is directed at arriving at a determination concerning a positional state of the examination object relative to the positioning apparatus based on the region of interest and the object information. A further step is directed at the provision of user output for a user of the imaging system based on the determination.

The medical imaging system can be generally embodied to record medical image data from the examination object. For this purpose, the imaging system can include one (or more) imaging unit embodied to map the examination object or one or more sections of the examination object with medical imaging methods. Medical imaging methods can be based on X-ray fluoroscopy, computed tomography (CT), magnetic resonance tomography (MR), and/or positron emission tomography (PET). Accordingly, the imaging unit can include a computed tomography device, a C-arm X-ray device, a magnetic resonance tomography device, and/or a positron emission tomography device. The image data of the examination object generated by the imaging unit can, for example, be two-dimensional with two spatial dimensions, three-dimensional with three spatial dimensions or two spatial dimensions and one temporal dimension, or four-dimensional with three spatial dimensions and one temporal dimension.

The examination object can, for example, be embodied as an anatomical body with one or more cavities. In particular, the examination object can be a patient.

The positioning apparatus is embodied to accommodate and position the examination object. The positioning apparatus can further be embodied to move the examination object accommodated thereupon relative to the imaging unit. The positioning apparatus can in particular be a patient positioning apparatus for accommodating a patient. For example, the positioning apparatus can include a patient couch, such as, for instance, a surgical table. The positioning apparatus can further include a moving device for moving the patient couch relative to the imaging unit.

The object information can be understood as information specific to the respective examination object. In particular, the object information can be relevant for the examination to be performed on the examination object by the imaging unit. In other words, the object information can be object-specific (patient-specific) information that may need to be taken into account during the examination to be performed and in particular may influence the way in which the examination object is to be arranged on the positioning apparatus. The object information can in particular describe a geometry (one or more geometric properties) of the examination object. For example, the object information can comprise a body height or a body circumference.

The region of interest is the region of the examination object that is to be subject to an examination by the imaging unit. In other words, the examination can consist in that image data is to be recorded from the region of interest by the imaging unit. Herein, the region of interest can depend both on the planned examination per se and the geometry of the examination object. For example, the region of interest can be defined as the thorax region of the examination object if, for example, the chest cavity of a patient is to be mapped. As a further example, the region of interest can indicate, that in particular a rear side of the lung is to be mapped. The region of interest can describe a two-dimensional subarea or a three-dimensional subspace of the examination object. If, for example, a whole-body scan is to be performed, the region of interest can also correspond to the entire examination object. Thus, the type of examination to be performed has an influence on the region of interest.

The region of interest in turn determines which positional states of the examination object relative to the positioning apparatus are suitable for the examination to be performed and which are less suitable. Furthermore, a suitable positional state depends on the specific object information which can result in further constraints for the positional state. Herein, the positional state of the examination object can be understood as the position of the examination object relative to the positioning apparatus (and in particular to the patient couch and the lying surface thereof). The positional state can describe how (anatomical) landmarks are, or should be, arranged relative to the positioning apparatus. In the case of patients as examination objects, such landmarks can in particular be the contour (silhouette, outline) or body parts of the patient, i.e. for example head, eyes, thorax, chest, legs, joints etc. The positional state can further relate to an orientation of the examination object. The orientation can in particular comprise the relative orientation of the head and feet with respect to the patient couch or the position of the patient, i.e. for example supine position, lateral position right, lateral position left, prone position etc.

The determination concerning the positional state can be understood as a statement regarding an existing instantaneous positional state or as a statement regarding a positional state to be assumed. The determination can include both an evaluation of an (existing) positional state and the calculation of a (to-be-assumed) positional state. Herein, the determination is based on the above-described influencing factors: object information and region of interest. In other words, the determination is a result ascertained based on the input variables object information and region of interest and from which an effect on or statement about the (to-be-assumed or instantaneous) positional state can be derived. In other words, the determination can be applied to the positional state or implemented in relation to the positional state. According to one embodiment, the determination concerning the positional state can be understood as a determination of a positional state suitable for the examination to be performed based on the object information and the region of interest.

Finally, the determination is used as the basis for the generation of user output that can be provided to the user via a suitable user interface. The user can, for example, be an operator of the imaging system, such as, for example a physician or a technician. The user can further be the patient. The user output transfers the determination in a form that the user can develop, apply and implement thereby enabling the user to exert a targeted influence on a positional state to be assumed or act on an instantaneous positional state. The user interface can, for example, be embodied as a graphical user interface with one or more buttons, a projection arrangement, one or more lighting facilities, one or more loudspeakers, etc.

The aforementioned features interact synergistically in such a way that individual influencing factors on the positional state of an examination object are systematically and automatically taken into account during a medical imaging examination. The fact that both object information and the region of interest are evaluated means that object-specific properties are also taken into account, as well as the type of examination to be performed. Taking these parameters into account enables an individual determination regarding the positional state to be arrived at for each examination and for each examination object, whereby suitable positional states can be determined more quickly and unfavorable positional states can be corrected more efficiently. Further, the user output forwards the result of the analysis directly to the user of the imaging system thus enabling the user to react accordingly. This enables examination processes with unfavorable positional states to be effectively avoided, which can significantly reduce incorrect measurements and thus contribute to the reduction of the patient's radiation exposure according to the object of the invention as well as to improved efficiency in the use of the imaging system.

According to one embodiment, the object information can include information regarding the instantaneous positional state of the examination object relative to the positioning apparatus.

According to one embodiment, the instantaneous positional state can be ascertained by a sensor facility embodied to detect the instantaneous positional state.

The ascertainment of the instantaneous positional state enables this to be taken into account when arriving at the determination which, for example, opens up the possibility of evaluating or correcting the instantaneous positional state, in particular by comparison with a suitable positional state. Thus, the provision of user input based thereupon enables, for example, a positional state that is unsuitable for the examination to be performed to be identified and for this to be notified to the user. This can prevent incorrect measurements. Herein, an unsuitable instantaneous positional state can, for example, be defined as a misalignment of the examination object relative to the positioning apparatus, which prevents the region of interest being scanned by the imaging unit.

According to one embodiment, the object information includes information regarding one or more geometric properties of the examination object. Herein, the geometric properties can generally relate to dimensions of the examination object. For example, the geometric properties can include the (body) height, the (body) circumference, the position of one or more anatomical landmarks of the examination object, dimensions of parts of the examination object, such as, for example, the torso length or the circumference of the abdomen or chest. Herein, the position of the one or more anatomical landmarks can include a plurality of anatomical landmarks relative to one another—for example the hip-to-head distance. The position of the one or more landmarks can further comprise the absolute position of the landmarks in relation to the examination object.

The landmark or landmarks can in particular be a region of the patient's body, i.e. for example, the head, the eyes, the thorax, the chest, the legs or a single knee joint. In at least one embodiment of the invention, the determination of the position of the landmark(s) also comprises determining the relative position of a plurality of identified landmarks to one another. Furthermore, the identity and position of further landmarks can be inferred from landmarks that have already been identified. For example, the position of the heart or a lung can be inferred from the position and orientation of the thorax.

According to one embodiment, the arrival at a determination concerning the positional state comprises determining one or more anatomical landmarks of the examination object in the coordinate system of the positioning apparatus.

"Relating" anatomical landmarks to the coordinate system of the positioning apparatus enables an existing positional state to be evaluated quickly and easily from a technical point of view. Similarly, such an approach facilitates the specification of a suitable positional state to be assumed and the provision of the user output.

According to one embodiment, the geometric properties can be ascertained by a sensor facility embodied to provide this information. Additionally or alternatively, the geometric properties can be ascertained by querying a database, for example an information system in which the one or more examination object-related geometric properties, for example from previous examinations, are stored. Such an information system can, for example, be a hospital information system (HIS) or radiology information system (RIS) or another suitable database.

Taking account of the specific geometric properties of the examination object enables the determination concerning the positional state to be better adapted to the geometry of the examination object. For example, the body height and/or body circumference of the examination object can be taken into account during the determination, whereby an evaluation or calculation of a positional state can be individually adapted to the physiological conditions of the examination object.

According to one embodiment, the object information includes information regarding one or more constraints relevant to the examination of the examination object. Constraints relevant to the examination relate to information beyond the aforementioned geometric properties, which cannot be determined, or can only be determined with difficulty, by measuring the examination object via a sensor facility, but which could possibly influence the positioning of the examination object on the positioning apparatus. In particular, such constraints can relate to psychosomatic restrictions of the examination object, such as restricted mobility of one or more body parts, claustrophobic impairments, possible states of confusion, the degree of anesthesia or the responsiveness of a patient. Further constraints relevant to the examination can result from the need for ventilation/dialysis or the administration of contrast medium during the examination.

According to one embodiment, these constraints relevant to the examination can be ascertained by querying an aforementioned database, in particular by querying an aforementioned information system.

Taking account of constraints relevant to the examination enables the determination concerning the positional state to be even better adapted to the circumstances of the examination object and the examination to be performed. For example, this enables account to be taken of the fact that, if possible, a claustrophobic patient should not be pushed head-first into the opening of a gantry or that the need for ventilation requires an adapted positioning state.

According to one embodiment, the arrival at the determination comprises calculating a suitable positional state of the examination object relative to the positioning apparatus.

Depending on the object parameters and the region of interest, this in particular enables a suitable positional state to be determined proactively, i.e. before the examination object is arranged on the positioning apparatus. This can then be communicated to the user via the user output thus enabling the user to position the examination object in an equally suitable manner on the positioning apparatus. Moreover, the suitable positional state can be used to evaluate an already existing positional state by comparing it with the suitable positional state.

According to one embodiment, the user output comprises an instruction to assume the suitable positional state.

According to one embodiment, the arrival at the determination comprises an evaluation of an instantaneous positional state of the examination object relative to the positioning apparatus.

The evaluation of an instantaneous positional state opens up the possibility of influencing an already existing arrangement of the examination object on the positioning apparatus.

If the user is notified of the evaluation via the user output, the user can correct an unfavorable instantaneous positional state.

According to one embodiment, the evaluation of the instantaneous positional state comprises an ascertainment of an instruction to correct the instantaneous positional state, wherein the user output contains the instruction to perform a correction.

According to one embodiment, the positioning apparatus comprises a predetermined travel range relative to the imaging unit. The arrival at the determination is additionally based on the travel range.

Taking account of the travel range enables a better estimation to be made as to whether a positional state is suitable for the examination to be performed, i.e. for the region of interest to be scanned. For example, it may be the case that the travel range is not sufficient to move the examination object far enough in the direction of the imaging unit if it is positioned unfavorably on the positioning apparatus. Taking account of the travel range enables a more accurate statement to be made regarding the positional state.

According to one embodiment, the imaging unit includes a predetermined scanning range. The arrival at the determination is additionally based on the scanning range.

Taking account of the scanning range enables an improved estimation to be made as to which positional states are suitable for the examination to be performed and the examination object, and which are not suitable. Herein, the scanning range can in particular be taken into account in conjunction with the travel range which provides a complete image of the maximum relative movement possibilities within the imaging system.

According to one embodiment, the arrival at a determination comprises a statement as to whether the region of interest can be brought into complete overlap with the scanning range.

In this way, it can be ensured that the region of interest can also actually be scanned completely with a specified positional state.

According to one embodiment, in the step of the determination of the region of interest, the region of interest is determined based on the object information.

This is based on the realization that the region of interest depends not only on the examination to be performed, but also on the individual circumstances of the examination object. If, for example, a thorax scan is to be performed, the region of interest will be embodied differently depending on the body height, torso length and/or torso circumference. This is taken into account by dynamically determining the region of interest in dependence on the object information. Thus, the actual region of interest can be better estimated when determining a suitable positional state which allows a more accurate statement regarding the positional state.

According to one embodiment, the method further includes the step of receiving examination information from a database or from an information system and the step of determining the region of interest takes place based on the examination information.

The examination information can in particular comprise information about the type of examination planned for the examination object. For example, the examination information can hold the information that a head scan is to be performed for the patient X. Hence, the examination information can be understood as basic information for determining the region of interest. As stated above, on this basis, the determination of the region of interest can be further refined by taking account of the object information. The information system can, for example, be embodied as a hospital information system (HIS) or radiology information system (RIS) and in particular contain an examination planning module. The reception of the examination information enables the region of interest to be determined automatically without requiring user input, which improves the user-friendliness of the system. Alternatively, the examination information can be prespecified by a user input.

According to one embodiment, the user output includes an optical and/or acoustic instruction for positioning the examination object on the positioning apparatus.

Herein, the instruction can relate to both a positional state to be assumed and an instantaneous already existing positional state. The optical and/or acoustic instruction can include an instruction for positioning and/or correcting positioning of the examination object on the positioning apparatus. The acoustic instruction can be embodied as voice output containing one or more instructions and/or warnings to the user or an acoustic warning signal. The optical instruction can be provided to the user in the form of one or more light signals or via a suitable depiction unit, such as, for example, a display. The output of an optical and/or acoustic instruction concerning the positional state of the examination object on the positioning apparatus provides the user with intuitive support in finding a suitable positional state.

According to one embodiment, the user output includes an optical and/or acoustic warning signal in the event of an unfavorable positional state.

According to one embodiment, the user output is projected onto the positioning apparatus and/or the examination object accommodated thereupon via a projection arrangement.

The projection of the user output directly onto the positioning apparatus or onto the examination object allows a depiction of a suitable positional state or of how an existing positional state should be corrected if necessary, which is easily accessible for the user.

According to one embodiment, the user output is depicted to the user via a depicting facility, in particular comprising one or more displays.

According to a further embodiment, the method according to the invention comprises the calculation of a patient model based on a three-dimensional contour of the examination object for depicting an image of the examination object. Such a model can be easily modified, for example the corresponding depiction of the image can take place from different viewing angles so that a user of an imaging system according to the invention or a person providing the treatment can take account of the information of the three-dimensional contour when planning the positioning or further treatment. According to one embodiment, the user output is provided based on the three-dimensional contour. In particular, the user output includes the three-dimensional contour and a schematic depiction of the patient-positioning apparatus such that the positional state of the examination object is reproduced. Such user output is advantageously depicted with a depicting facility, in particular comprising one or more displays.

According to a further embodiment of the present invention, a medical imaging system is provided. The medical imaging system includes an imaging unit, a positioning apparatus for positioning an examination object, and a processing unit. Herein, the processing unit is embodied to determine object information on the examination object. The processing unit is further embodied to determine a region of interest, wherein the region of interest is defined as a region of the examination object to be examined by the imaging unit. The processing unit is further embodied, based on the object information and the region of interest, to arrive at a determination relating to a positional state of the examination object on the positioning apparatus. Furthermore, the processing unit is embodied to generate user output based on the determination.

The processing unit can be embodied as a centralized or decentralized controller of the imaging system. The processing unit can include one or more control devices and/or one or more processors. The processing unit can be implemented as a local or cloud-based processing server. The processing unit can advantageously include at least one user interface. The user interface can include an input element, for example a keyboard and/or a joystick and/or a capacitive and/or resistive input panel, which enables the imaging system to be controlled by a user through a corresponding operator input. The user interface can further include a depicting element, for example a monitor or a display. The depicting element can be embodied for the graphical depiction of one or more results of the determination regarding the positional state for a user.

The advantages of the suggested imaging system substantially correspond to the advantages of the suggested method. Features, advantages or alternative embodiments can also be transferred to the other claimed subject matter and vice versa.

According to one embodiment, the medical imaging system further includes a sensor facility embodied to provide the object information, in particular by measuring the examination object.

The provision of a sensor facility enables one or more items of the aforementioned object information to be ascertained directly on the examination object thus enabling the accurate detection of current data.

The sensor facility can be embodied to scan at least part of the surface of the examination object. In particular, the sensor facility can be embodied to scan at least part of the surface of the examination object in a contactless manner. The sensor facility can include at least one electromagnetic sensor embodied for the aforementioned tasks. The sensor facility and/or the processing unit can in particular be embodied to calculate a three-dimensional contour of the scanned surface. The sensor facility and/or the processing unit can in particular be embodied to ascertain one or more anatomical landmarks based on the scanned surface, in particular based on the calculated contour.

Herein, the measurement of the examination object can in particular take place via optical measuring methods. According to one embodiment, for this purpose, the sensor facility can include an optical measuring facility. The optical measuring facility can, for example, be embodied in the form of a camera facility and/or a triangulation system and/or a laser-scanning facility. Herein, the camera facility can in particular include a 3D-camera facility such as a stereo camera system embodied to detect a three-dimensional image of the examination object. The laser-scanning facility can also generate a three-dimensional model of the examination object by time-of-flight measurement of emitted and re-detected laser beams. The laser-scanning facility can in particular be embodied as a LIDAR system. The optical measuring facility can further include a time-of-flight measuring system ("time-of-flight camera"). In a further embodiment, the optical measuring facility can be embodied to scan a surface via structured lighting. One advantage of the aforementioned optical measuring systems lies in a comparatively quick and equally accurate detection of basic geometric properties. The optical measurement of the examination object can be followed by further processing steps. Such processing steps can, for example, include image data evaluation methods for the image data recorded with the camera facility in order, for example to extract the three-dimensional contour of the examination object, dimensions or the position of one or more anatomical landmarks of the examination object.

A conceivable alternative to optical measurement of the examination object is measurement based on contact with the examination object. According to one embodiment, the sensor facility can, for example, include a pressure-sensitive sensor facility. This pressure-sensitive sensor facility can, for example, be embodied as a pressure-sensitive mat which is arranged on the positioning apparatus and embodied to determine the object information (in particular one or more geometric properties of the examination object) from the pressure load exerted by the examination object.

According to a further embodiment, the sensor facility can include a combination of one or more of the aforementioned components, which creates redundancies and ensures reliable detection of the object information. For example, within the sensor facility, a camera facility and/or laser-scanning facility can be combined with a pressure-sensitive sensor facility.

According to one embodiment, the medical imaging system further includes a projection arrangement embodied to project graphical information onto the positioning apparatus and/or the examination object accommodated thereupon. The processing unit is embodied to project the user output onto the positioning apparatus and/or the examination object accommodated thereupon via the projection arrangement. The projection arrangement can in particular include a light-projecting arrangement embodied for the directed emission of one or more light signals. For example, the projection arrangement can include: one or more video projectors ("beamers"), one or more lighting facilities, such as light strips, one or more laser projectors or any combination of the aforementioned components.

In a further embodiment, the invention relates to a computer program product which comprises a program and can be loaded directly into a memory of a programmable computing unit and includes program segments, for example libraries and auxiliary functions, in order to execute a method to control an imaging system in particular according to the aforementioned embodiment when the computer program product is executed.

Herein, the computer program product can comprise software with a source code which still has to be compiled and linked or only has to be interpreted or an executable software code that only needs to be loaded into the processing unit for execution. The computer program product enables the method to be executed quickly, identically repeatedly and robustly. The computer program product is configured such that it can execute the method steps according to the invention via the processing unit. Herein, the processing unit must in each case fulfil the requisite conditions such as, for example, an appropriate random-access memory, an appropriate graphics card or an appropriate logic unit so that the respective method steps can be executed efficiently.

The computer program product is, for example, stored on a computer-readable medium or held on a network or server from where it can be loaded into the processor of a processing unit, which can be directly connected to the processing unit or embodied as part of the processing unit. Furthermore, control information of the computer program product can be stored on an electronically readable data carrier. The control information of the electronical readable data carrier can be embodied to perform a method according to an embodiment of the invention when the data carrier is used in a processing unit. Examples of electronically readable data carriers are a DVD, a magnetic tape or a USB stick on which electronically readable control information, in particular software, is stored. When this control information is read from the data carrier and stored in a processing unit, all embodiments according to the invention of the above-described methods can be performed. For example, the invention can also be based on the computer-readable medium and/or the electronically readable data carrier. The advantages of the suggested computer program product substantially correspond to the advantages of the suggested methods.

FIG. 1 shows an example imaging system 1 according to an embodiment of the invention. During the recording of an image data set, the patient 5 (the examination object) lies on a patient couch 6, which is connected to a couch base 16 such that the couch base 16 supports the patient couch 6 with the patient 5. The patient couch 6 and bench base 16 can together form the positioning apparatus 6, 16. The patient couch 6 can move the patient 5 in a horizontal direction along the system axis 17 and in a vertical direction perpendicular thereto. With some patient couches, however, these two directions of travel cannot be adjusted completely independently of one another in different situations. This makes it very difficult for the operator to estimate whether or not the planned target position is within the limits of the travel paths.

The imaging system 1 shown in FIG. 1 includes by way of example a CT device 7. During a tomographic recording of an X-ray image, an X-ray detector 9 and an X-ray source 8 interacting with the X-ray detector 9 move about a system axis 17. The X-ray source 8 and X-ray detector 9 are arranged in a gantry 19 such that they face one another and the X-rays 20 from the X-ray source 8 can be detected by the X-ray detector 9. As depicted in FIG. 1, the X-ray detector 9 can be a detector with a plurality of rows and columns. In a further embodiment, the CT device 7 can in each case have two pairs of X-ray sources 8 and X-ray detectors 9 which interact with one another so that the CT device 7 is particularly suitable for multi-energy recordings.

During a recording, the patient 5 is moved along the system axis 17 through the opening 18 of the gantry 19 of the CT device 7. During this movement, multiple projection recordings of a body part of the patient 5 are created. Such interaction between the positioning apparatus 6, 16 and the CT device enables a region of interest UB of the patient 5 to be scanned or imaged. Herein, the region of interest UB depends upon the scanning range of the CT device, the travel range of the patient couch 6 and the positional state of the patient 5 relative to the patient couch 6.

Although, in the present example embodiment, a CT device 7 is depicted as an imaging unit of the imaging system 1, the imaging system 1 can also include other or further imaging units, for example a C-arm X-ray device, a magnetic resonance tomography device (MR) and/or a positron-emission tomography device (PET).

Furthermore, the imaging system 1 according to an embodiment of the invention can have at least one sensor facility 31. The sensor facility 31 is embodied to determine object information relating to the patient 5. Such object information can, for example, be the body height, body circumference or the positional state of the patient 5 relative to the patient couch 6.

The sensor facility 31 can be embodied for contactless scanning of at least part of the surface of the patient 5. For this purpose, the sensor facility 31 can be embodied to detect electromagnetic radiation, in particular to detect electromagnetic radiation in a low-frequency spectral range compared to X-rays, for example in the visible or infrared spectral range. For example, the sensor facility 31 can be one or more photographic cameras or one or more video cameras. In the example shown here, the sensor facility 31 is a 3D camera mounted on the gantry embodied, for example, as a stereo camera or as a time-of-flight system ("time-of-flight camera"). In a further embodiment of the invention, the sensor facility 31 can be embodied to scan a surface via structured lighting. In this embodiment, the imaging system 1 additionally includes a lighting unit for generating structured lighting of at least part of the surface of the patient 5. Furthermore, in this case, the sensor facility 31 and the lighting unit are positioned and embodied in their emission or detection properties such that the sensor facility 31 is embodied to detect the radiation reflected from the surface of the patient 5.

In a further embodiment of the invention, the sensor facility 31 is permanently integrated in the gantry 19 of the CT device 7. In an alternative embodiment, the sensor facility 31 is integrated in the rotatable part of the gantry 19 such that the sensor facility 31 rotates with the X-ray source 8 or the X-ray detector 9 during recording. This enables the surface of the patient 5 to be scanned particularly easily and quickly from different perspectives. The sensor facility 31 can furthermore be positioned somewhere else in the room in which the CT device 7 is located, for example it can be attached to or suspended from the ceiling or placed on a stand such as a tripod. For example, the sensor facility 31 can be positioned centrally above the patient 5 or centrally above the patient couch 6. In principle, it is advantageous for the sensor facility 31 to be positioned such that the quality of the depth information relative to the scanned surface of the patient 5 is as homogeneous as possible. The noise or error in depth information ascertained by scanning or subsequently calculated contour information should depend as little as possible on the actual depth information or contour information or the position of the scanned region.

According to one embodiment, the sensor facility 31 can also be embodied to ascertain the object information by pre-scanning the patient 5 at a point in time before the patient 5 is arranged on the patient couch 6, for example, when the patient enters the examination room or is standing next to the CT device 7.

According to a further embodiment, the sensor facility can also be embodied as a touch-sensitive sensor facility (not depicted), for example as a touch-sensitive mat arranged on the patient couch 6. Such a mat can include one or more pressure sensors the position of which can advantageously be registered with the patient couch 6. This enables the relative positional state of the patient 5 with respect to the patient couch 6 to be ascertained in addition to the body length and body circumference.

In addition, the imaging system 1 according to an embodiment of the invention can have a projection arrangement 32. The projection arrangement 32 is in particular embodied to project user output onto the patient couch 6 or the patient 5 accommodated thereupon. For this purpose, the projection arrangement 32 can be positioned centrally above the patient 5 or centrally above the patient couch 6. For example, the projection arrangement 32 can be attached to or suspended from the ceiling. The projection arrangement 32 can furthermore be positioned somewhere else in the room in which the CT device 7 is located, for example it can be placed on a stand such as a tripod. In addition, similarly to the sensor facility 31, the projection arrangement 32 can be permanently arranged on the CT device 7. For example, the projection arrangement 32 can be permanently integrated into the gantry 19.

If the sensor facility 31 and projection arrangement 32 are arranged at the same position, the sensor facility 31 and projection arrangement 32 can be accommodated in a common housing which can increase the modularity of the arrangement and reduce component costs. In addition, the projection arrangement 32 can also be embodied as the aforementioned lighting unit. Conversely, the lighting unit can be embodied as the projection arrangement 32. The projection arrangement 32 can include a beamer, a laser projection unit, a light strip, one or more LED lights, etc.

According to one embodiment, the imaging system 1 further includes a processing unit 20 with a wired or wireless data connection to the system components (i.e. in particular the imaging unit 7, the patient-positioning apparatus 6, 16, the sensor facility 31 and/or the projection arrangement 32). The processing unit 20 can be embodied as a central control unit, for example as a control device with one or more processors. Alternatively, the processing unit 20 can be embodied as part of the imaging unit 7. As a further embodiment, the functionalities of the processing unit 20 described below can also be distributed in a decentralized manner between a plurality of computing units or control devices.

The processing unit 20 can further include a user interface 21, 22. The user interface 21, 22 can include an input element 21, for example a keyboard and/or a depicting unit 22, for example a monitor and/or display. Herein, the input element 21 can be integrated in the depicting unit 22, for example in the form of a capacitive and/or resistive input display. The depicting unit 22 can be embodied to display information and/or graphical depictions of information, in particular user output concerning the positional state of the patient 5 relative to the patient couch 6, for example in a graphical user interface GUI.

The imaging system can further include a storage unit 23 or be in data connection with such a unit. The storage unit 23 can be embodied as a centralized or decentralized database. The storage unit 23 can in particular be part of a server system. The storage unit 23 can in particular be part of a hospital or radiology information system (HIS or RIS). The storage unit can in particular be part of a scheduling system for occupancy planning of the imaging system 1 or include a corresponding planning module for occupancy planning. The storage unit 23 can in particular be embodied such that patient information (object information) specific to the patient 5 to be examined can be retrieved therefrom. The patient information can contain patient parameters relevant to the examination (for example body height, body circumference, torso length, gender etc.), patient-constraints (for example psychosomatic restrictions such as claustrophobic anxiety, restrictions of the locomotor system, etc.) and/or a reference to the examination to be performed on the patient 5 by the imaging unit 7 (for example in the form of examination information) from which the region of interest can be derived.

Data connections between system components (for example the imaging unit 7, patient positioning apparatus 6, 16, processing unit 20 and/or storage unit 23) can take place via one or more suitable data interfaces, which can include a hardware and/or software interface, for example a PCI bus, a USB interface, a FireWire interface, a ZigBee interface or a Bluetooth interface. The data interfaces can include an interface of a communication network, wherein the communication network can include a local area network (LAN), for example an intranet or a wide area network (WAN). Accordingly, the one or more data interfaces can include a LAN interface or a wireless LAN interface (WLAN or WiFi).

Figure 2:
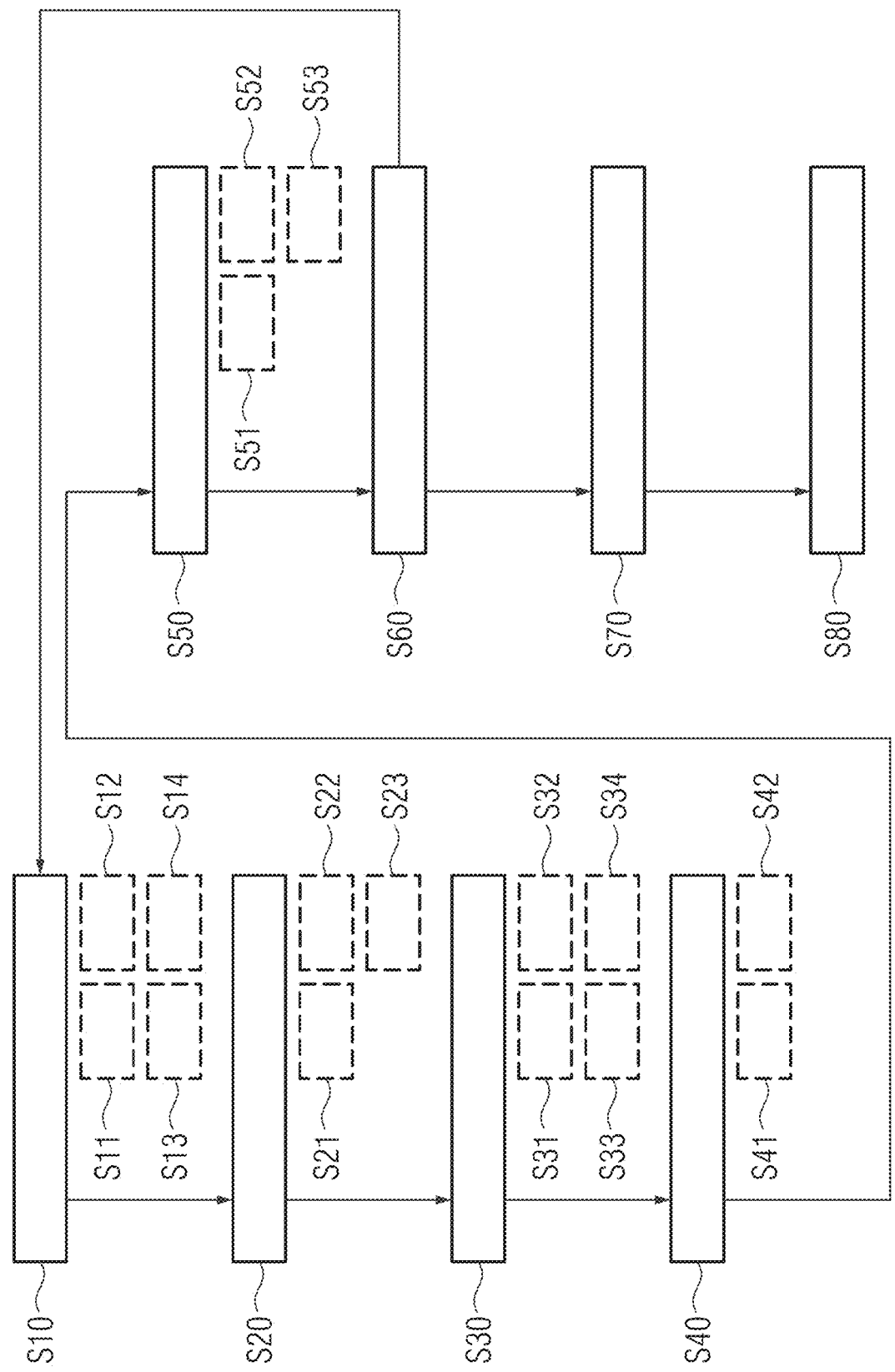

FIG. 2 shows a schematic depiction of an embodiment of the suggested method for operating a medical imaging system 1. The sequence of the method steps is not restricted by either the sequence depicted or the numbering selected. For example, the sequence of the steps can optionally be interchanged and individual steps can be omitted.

Step S10 is directed at ascertaining object information relating to the patient 5. For this purpose, a storage unit 23, such as, for example, a hospital or radiology information system and/or a scheduling system for occupancy planning of the imaging system can be queried in an optional substep S11. To this end, for example, an electronic patient record for the patient 5 with a suitable electronic identifier (for example via the patient's name or the patient's ID) can be retrieved and automatically searched for object information. Alternatively or additionally, object information can also be held in the scheduling system and queried accordingly. The object information is ascertained via the sensor facility 31 by scanning the examination object 5 in an optional substep S12. Substep S12 can take place before or after the patient 5 has been arranged on the positioning apparatus 6, 16. In a further optional substep S13, a three-dimensional contour of the patient 5 is calculated based on the scanning result. Furthermore, one or more anatomical landmarks of the patient 5 can be calculated in a further optional substep S14. These anatomical landmarks are preferably calculated based on the three-dimensional contour and in the coordinate system of the positioning apparatus 6, 16 (in particular the patient couch 6).

The position of the anatomical landmarks in the coordinate system of the positioning apparatus 6, 16 (the patient couch 6) can be easily determined if a correlation between the coordinate system of the data recorded by the sensor facility 31 by scanning and the coordinate system of the positioning apparatus 6, 16 or the CT device 7 is known. Such a correlation can be ascertained by calibration which can precede the method according to an embodiment of the invention.

A further step S20 is directed at the determination of the region of interest UB. For this purpose, a storage unit 23 in which information regarding the examination to be performed for the patient 5 is held can be queried in an optional substep S21. The storage unit 23 can, for example, be part of an information system or scheduling system. Alternatively or additionally, examination information can be provided to the system 1 in an optional substep S22 via a user input, for example via the user interface 21, 22. During the determination of the region of interest UB, object information from step S10 can be taken into account in a further optional substep S23. In particular, the region of interest UB can be adapted in substep S23 based on object information. Herein, the region of interest UB can be determined both in the coordinate system of the patient 5 and in the coordinate system of the positioning apparatus 6, 16 (in particular in the coordinate system of the patient couch 6).

A further step S30 is directed at arriving at a determination regarding the positional state. Depending upon whether or not the patient 5 is already located on the positioning apparatus 6, 16, this can entail the evaluation of an instantaneous positional state (optional substep S31) or the ascertainment of a suitable positional state to be assumed (optional substep S32). Herein, the object information and the region of interest UB can be taken into account in both step S31 and step S32. Herein, it is additionally possible to take account of further parameters specified by the system 1 which are relevant for the assessment of the positional state. For this purpose, the travel range of the positioning apparatus 6 relative to the CT device 7 (or to its scanning range) is queried in the optional substep S33 and taken into account when arriving at the determination regarding the positional state. In a further optional substep S34, the scanning range of the imaging system 7 is queried and taken into account when arriving at the determination regarding the positional state.

In a further step S40, the determination made in step S30 regarding the positional state is converted into user output which enables the user (i.e., for example, the operator or the actual patient 5) to implement the result of the determination (for example: a suitable positional state) accordingly during the arrangement of the patient 5 on the positioning apparatus 6, 16. In an optional substep S41, the user output relates to an output concerning an already existing instantaneous positional state. This output can comprise a warning to the effect that an unfavorable positional state is present in which the examination to be performed is not possible. The output can also, for example, include a correction prompt as to how the unfavorable positional state can be corrected. If, on the other hand, a suitable positional state is already present, the instruction can also consist in a confirmation of the instantaneous positional state. In an optional substep S42, the user output relates to an instruction as to how a patient 5 not yet arranged on the positioning apparatus 6 can be placed thereupon so that a suitable positional state can be assumed.

The optional step S50 is directed at the output of the user output. This output can take place as a projection P via a projection arrangement 32 (optional substep S51). Alternatively or additionally, the output can take place via a user interface 21, 22, such as, for example, a display (optional substep S52). Alternatively or additionally, the output can take place as acoustic output via an acoustic facility, such as, for example, a loudspeaker.

The optional step S60 is directed at a user changing or assuming a positional state. Herein, step S60 can in particular take place as a reaction to the user output in step S50 and implement instructions contained in the user output.

The optional step S60 is directed at repeating the steps S10-S30 or S40 and S50 (optionally including one or more optional substeps) after a change of the positional state has been detected.

The optional step S70 comprises approving the examination to be performed on the examination object 5 by the imaging unit 7 in dependence on the determination S30 regarding the positional state. In particular, step S70 comprises the approval of the examination to be performed if it has been determined in step S30 that a positional state of the examination object 5 relative to the positioning apparatus 6 that is suitable for the examination to be performed is present.

Finally, the optional step S80 is directed at the performance of the examination to be performed on the examination object 5 by the imaging unit 7.

FIGS. 3 to 10 are different schematic depictions of user outputs.

Figure 3:
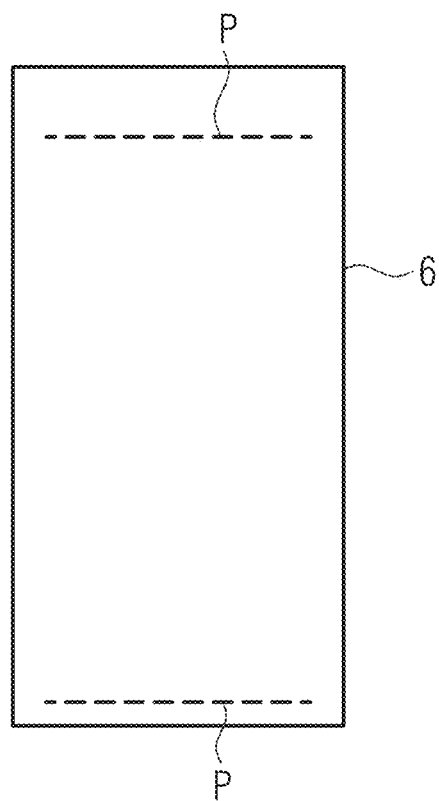
Figure 4:
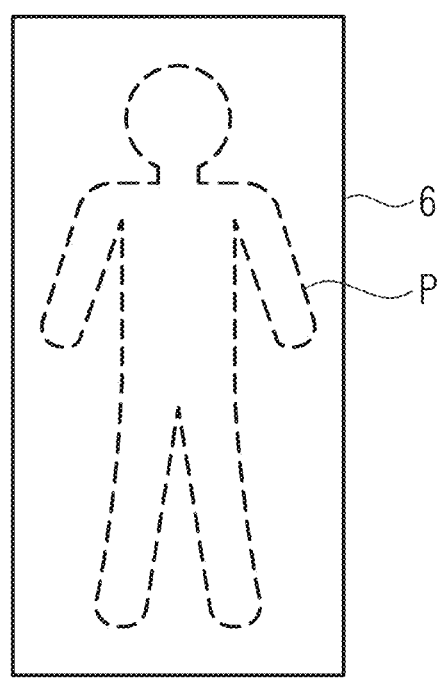

In FIGS. 3 and 4, an indication regarding an optimal positional state for the patient 5 is projected to the user with one or more projections P onto the patient couch 6. The projection P preferably takes place before the patient 5 gets onto the patient couch 6 so that the patient 5 can be correctly positioned from the start. Herein, the projections P can be generated by the projection arrangement 32. As shown in FIG. 3, the user output can be embodied to display an optimal positional state in the form of projected strokes or lines. Alternatively, the silhouette or contour of the patient 5 can be projected onto the patient couch 6 thus allowing an intuitively accessible depiction of the positional state. The projections P (and in particular the projection of the contour) can take account of patient parameters such as, for example, body height and circumference so that a projection P matching the patient 5 in terms of size can be generated.

Figure 5:
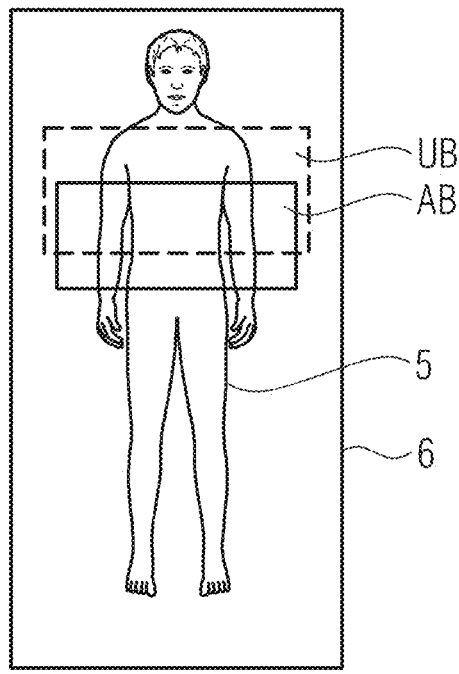
Figure 6:
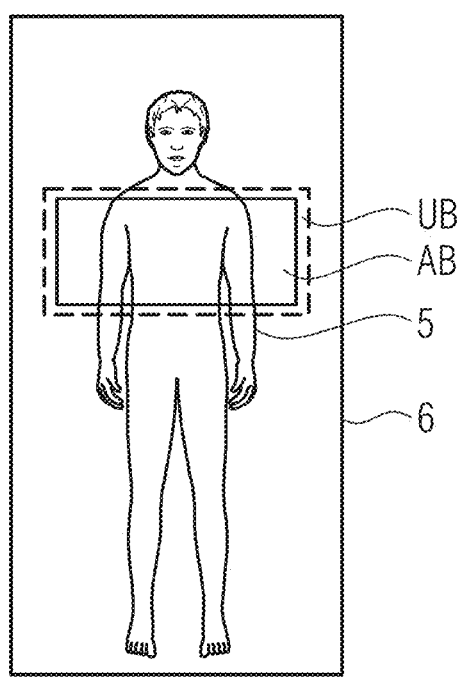

FIGS. 5 and 6 show example user outputs for correcting an instantaneous positional state of the patient 5. Therefore, the patient 5 is already lying on the patient couch 6. In FIGS. 5 and 6, the user output again takes place in the form of projections P onto the patient couch 6 and the patient 5 accommodated thereupon. As depicted in FIGS. 5 and 6, herein, suitable depictions of the region of interest UB and/or of the scanning range AB can be projected. Herein, for intuitive depiction, the scanning range is corrected by the (maximum) travel range of the patient couch 6 so that the position of the scanning range AB in the projection corresponds to the actual position of the scanning range AB when the patient 5 has been moved into the opening 18 of the gantry 19 in the current positional state. FIG. 5 shows the user that the scanning range AB cannot be brought into overlap with the region of interest UB. In other words, the patient 5 is too close to the head end of the patient couch 6. This enables the user to identify and correct a misalignment of the patient 5 immediately. If the positional state of the patient 5 relative to the patient couch 6 changes as the result of a correction, the relative positions of the region of interest UB and scanning range AB relative to the patient couch 6 are recalculated and the projections P are adjusted accordingly. In FIG. 6, the patient 5 is positioned to enable the desired scan of the region of interest UB to be performed. This is indicated to the user in that the region of interest UB overlaps with the scanning range AB in the projected depiction. Instead of a defined scanning range AB, in FIGS. 5 and 6, it is also possible for only a boundary line of the scanning range AB indicating a maximum extension of the scanning range AB to be used to be projected.

Figure 7:
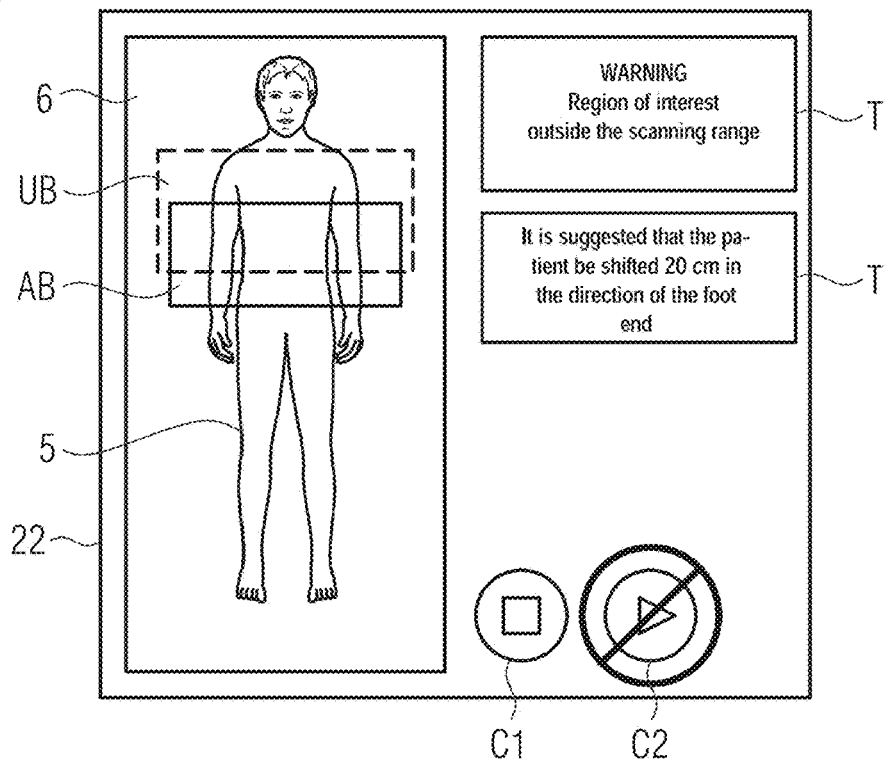
Figure 8:
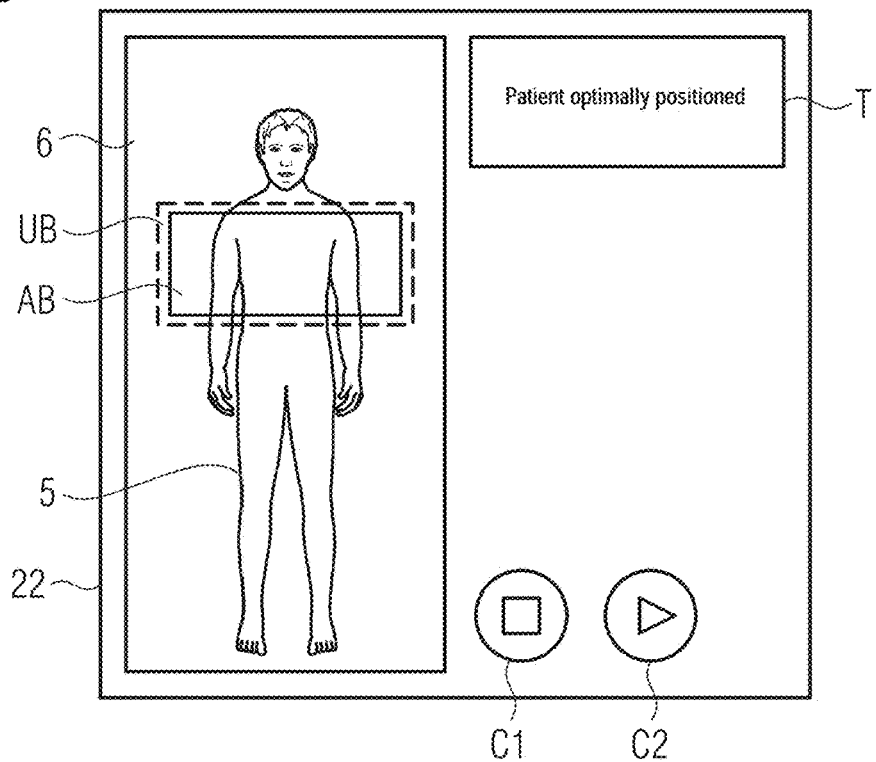

FIGS. 7 and 8 depict examples of graphical user outputs which can be depicted to the user as a graphical user interface (GUI) for example via the depicting unit 22. The graphical user output can include a schematic depiction, for example using the three-dimensional contour, of the patient 5 located on the patient couch 6. Alternatively, the graphical user output can include a real image recording of the patient 5 on the patient couch 6. As shown in FIGS. 7 and 8, schematic depictions of the region of interest UB and/or of the scanning range AB can be superimposed on the depiction of the patient. Similarly to that described in connection with FIG. 5, misalignment of the patient 5 can be evident by the fact that the region of interest UB cannot be brought into complete overlap with the scanning range AB (wherein the travel range is again taken into account appropriately in the depiction of the scanning range AB). As a further support, the user can be shown text messages T regarding the positional state. Herein, these may entail one or more warning messages indicating inadequate positioning of the patient 5 on the patient couch 6. In addition, the text messages T can include recommendations for action based on the instantaneous positional state, the region of interest UB, the travel range and/or the scanning range AB on how an improvement of the positional state can be brought about in order to perform the planned examination.

As depicted in FIGS. 7 and 8, the graphical user interface can further include operator control panels C1, C2 with which the imaging unit 7 can be operated. For this purpose, the depicting unit 22 can be embodied as a capacitive and/or resistive input panel. For example, a scan can be stopped or started via the operator control panels C1, C2. According to one advantageous embodiment, the start of the scan can be blocked via the operator control panels C1, C2 for as long as the positional state of the patient 5 on the patient couch 6 does not allow the scan to be performed. Alternatively, the operator control panels C1, C2 can also be embodied as operator control elements outside the graphical user interface. Nevertheless, these operator control elements can also be embodied in such a way that the performance of the examination via the imaging unit 7 is blocked if the positional state of the patient 5 does not permit the examination.

FIG. 8 depicts the graphical user interface for a case in which an acceptable positional state has been assumed in which the region of interest UB is compatible with the scanning range AB (possibly taking account of the travel range of the patient couch 6). The text warning and the text recommendation for action are replaced by a text message T confirming the correct positioning of the patient 5 on the patient couch 6. In addition, any blocking of the operator control panel C2 with respect to starting the examination can be cleared. In other words, the examination to be performed can be approved.

Figure 9:
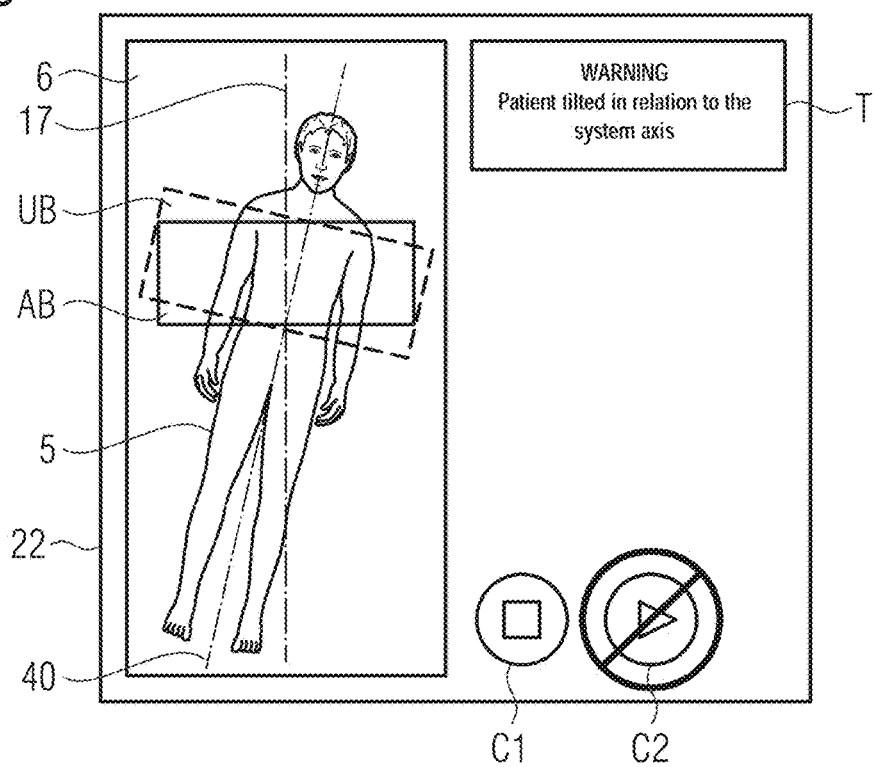
Figure 10:
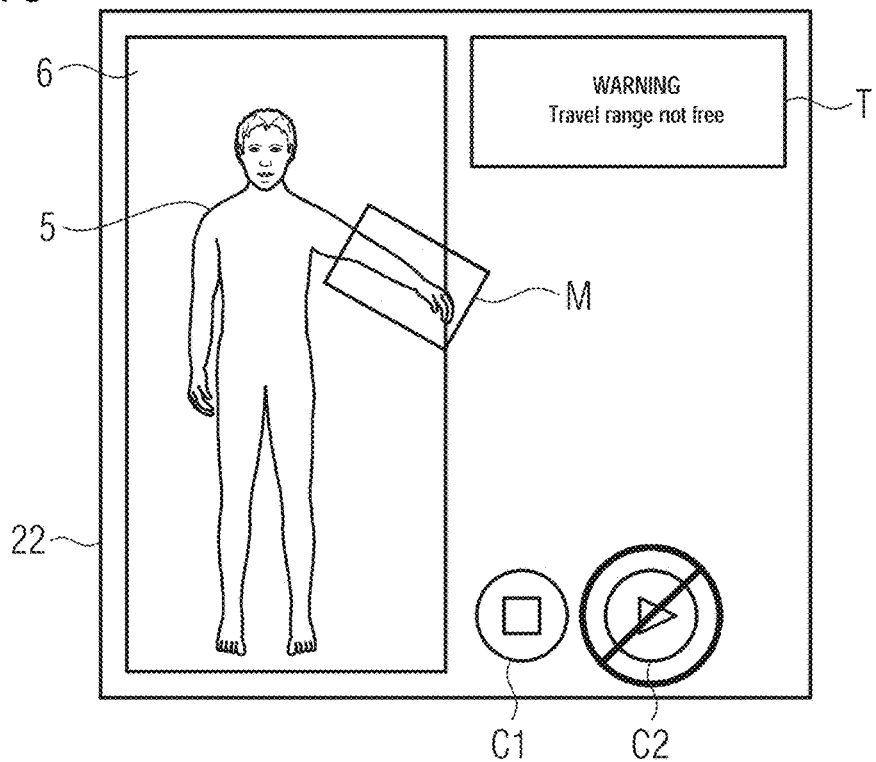

An incorrect positional state of the patient 5 on the patient couch 6 can further manifest itself in an inadequate alignment of the patient 5 with the system axis 17 or an unfavorably placed body part which could collide with the imaging unit 7 when the examination is performed while moving the patient couch. According to the invention, corresponding user inputs are also provided for such cases, such as, for example, depicted in FIGS. 9 and 10. As shown in FIG. 9, the system axis 17 and the patient axis 40 tilted with respect thereto can be graphically depicted (for example superimposed over a schematic or real image depiction of the patient 5). As depicted in FIG. 10, the graphical user interface further allows an unfavorably placed body part to be highlighted by a warning marker M (which can also be superimposed on the depiction of the patient). In addition, corresponding warnings and recommendations for action T in text format and the scanning range AB and region of interest UB can be inserted. The user outputs mentioned in connection with FIGS. 9 and 10 can of course be provided in an analogous manner by the projection arrangement 32 in the form of one or more projections P onto the patient couch 6 and/or the patient 5 located thereupon.

Alternatively or additionally to the visual user outputs depicted in FIGS. 3 to 10, the user outputs can also be of an acoustic nature. For example, a user can be provided with an acoustic warning as user output if, for example, the instantaneous positional state does not permit a scan. Such a user output can be embodied as a warning tone or voice message (text to speech). Furthermore, acoustic user outputs can include verbal instructions as to how an instantaneous positional state should be improved.

Finally, reference is made to the fact that the methods described in detail above and the apparatuses depicted are only example embodiments which can be modified by the person skilled in the art in a wide variety of ways without departing from the scope of the invention. Furthermore, the use of the indefinite article "a" or "an" does not preclude the possibility of the features in question also being present on a multiple basis. Similarly, the terms "unit" and "element" do not preclude the possibility of the components in question consisting of a plurality of interacting sub-components which optionally also may be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for operating a medical imaging system, the imaging system including an imaging device having a scanning range and a positioning apparatus to position an examination object, the method comprising:
   ascertaining object information relating to the examination object;
   determining a region of interest for the examination object, the region of interest being a region of the examination object to be examined by the imaging device in context of an examination to be performed;
   determining, prior to positioning the examination object on the positioning apparatus, a positional state of the examination object, relative to the positioning apparatus, based on the region of interest determined, the object information ascertained, and the scanning range, the determining the positional state including,
      determining whether or not the region of interest is bringable into complete overlap with the scanning range;
   providing user output, for a user of the imaging system, based on the determination of the positional state; and
   arranging the examination object on the positioning apparatus based on the user output.

2. The method of claim 1, wherein the object information includes at least one of:
- information regarding an instantaneous positional state of the examination object relative to the positioning apparatus;
- information regarding one or more geometric properties of the examination object; or
- information regarding constraints relevant to the examination relating to the examination object.

3. The method of claim 1, wherein the determining of the positional state includes at least one of:
- calculating a suitable positional state of the examination object relative to the positioning apparatus, or
- evaluating an instantaneous positional state of the examination object relative to the positioning apparatus.

4. The method of claim 1, wherein
the positioning apparatus has a travel range relative to the imaging device, and
the determining of the positional state is additionally based on the travel range.

5. The method of claim 1, wherein the determining of the region of interest takes place based on the object information.

6. The method of claim 1, further comprising:
receiving examination information regarding the examination to be performed from a database, wherein the determining of the region of interest is based on the examination information received.

7. The method of claim 1, wherein the user output includes at least one of an optical instruction or an acoustic instruction for positioning the examination object on the positioning apparatus.

8. The method of claim 1, wherein at least one of
the user output is projected onto the positioning apparatus; or
the examination object is accommodated onto the positioning apparatus via a projection arrangement.

9. The method of claim 1, wherein the user output includes at least one of an optical warning signal or an acoustic warning signal in an event of an unfavorable positional state.

10. A non-transitory computer program product storing a program, directly loadable into a memory of a programmable computing device, including program segments for executing the method of claim 1 when the program is executed in the computing device.

11. The method of claim 1, further comprising:
evaluating whether the positional state of the examination object relative to the positioning apparatus permits imaging of the examination object;
generating a correction prompt if the positional state does not permit imaging of the examination object; and
generating a confirmation prompt if the positional state permits imaging of the examination object.

12. The method of claim 2, wherein the determining of the positional state includes at least one of:
- calculating a suitable positional state of the examination object relative to the positioning apparatus, or
- evaluating an instantaneous positional state of the examination object relative to the positioning apparatus.

13. The method of claim 2, wherein
the positioning apparatus has a travel range relative to the imaging device, and
the determining of the positional state is additionally based on the travel range.

14. A medical imaging system, comprising:
an imaging device having a scanning range;
a positioning apparatus to position an examination object; and
at least one processor configured to
determine object information on the examination object,
determine a region of interest, the region of interest being defined as a region of the examination object to be examined by the imaging device during an examination to be performed,
determine, prior to positioning the examination object on the positioning apparatus, a positional state of the examination object, relative to the positioning apparatus, based on the object information, the region of interest determined, and the scanning range, wherein the at least one processor is further configured to determine whether or not the region of interest is bringable into complete overlap with the scanning range; and
generate user output based on the determination of the positional state, such that the examination object is arranged on the positioning apparatus based on the user output.

15. The medical imaging system of claim 14, further comprising:
a sensor facility configured to provide the object information by measuring the examination object.

16. The medical imaging system of claim 14, further comprising:
a projection arrangement configured to project graphical information onto at least one of the positioning apparatus or the examination object accommodated on the positioning apparatus;
wherein the at least one processor is further configured to project the user output onto at least one of the positioning apparatus or the examination object accommodated on the positioning apparatus, via the projection arrangement.

17. The medical imaging system of claim 15, wherein the sensor facility includes at least one of a camera facility, a laser-scanning facility, or a pressure-sensitive sensor facility.

18. The medical imaging system of claim 15, further comprising:
a projection arrangement configured to project graphical information onto at least one of the positioning apparatus or the examination object accommodated on the positioning apparatus;
wherein the at least one processor is further configured to project the user output onto at least one of the positioning apparatus or the examination object accommodated on the positioning apparatus, via the projection arrangement.

* * * * *